(12) United States Patent
Shibata et al.

(10) Patent No.: US 8,897,533 B2
(45) Date of Patent: Nov. 25, 2014

(54) MEDICAL IMAGE PROCESSING APPARATUS

(71) Applicants: Mariko Shibata, Nasushiobara (JP); Yasuo Sakurai, Nasushiobara (JP); Shigeharu Ohyu, Yaita (JP)

(72) Inventors: Mariko Shibata, Nasushiobara (JP); Yasuo Sakurai, Nasushiobara (JP); Shigeharu Ohyu, Yaita (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/679,380

(22) Filed: Nov. 16, 2012

(65) Prior Publication Data
US 2013/0070998 A1    Mar. 21, 2013

Related U.S. Application Data

(63) Continuation of application No. PCT/JP2011/074932, filed on Oct. 28, 2011.

(30) Foreign Application Priority Data

Oct. 29, 2010 (JP) ................ 2010-243089

(51) Int. Cl.
*G06K 9/00* (2006.01)
*G06T 1/00* (2006.01)
*G01N 1/00* (2006.01)
*A61B 16/00* (2006.01)
*G06T 7/00* (2006.01)
*A61B 6/00* (2006.01)
*A61B 5/05* (2006.01)
*A61B 6/03* (2006.01)

(52) U.S. Cl.
CPC .............. *G06T 7/0012* (2013.01); *G06T 1/00* (2013.01); *G01N 1/00* (2013.01); *A61B 6/5217* (2013.01); *A61B 6/505* (2013.01); *A61B 6/032* (2013.01); *A61B 16/00* (2013.01)
USPC .................. 382/131; 378/4; 378/8; 600/425

(58) Field of Classification Search
CPC ..................................... G06K 9/00; G06T 1/00
USPC ............. 382/103, 128–134; 378/4, 8, 21–27, 378/101, 901; 600/407, 410, 411, 425, 427; 128/920, 922
See application file for complete search history.

(56) References Cited

U.S. PATENT DOCUMENTS

| 6,011,862 A  * | 1/2000 | Doi et al. ................ 382/132 |
| 8,520,915 B2 * | 8/2013 | Ohyu et al. .............. 382/128 |
| 2005/0051065 A1* | 3/2005 | Hierholzer ................ 110/341 |

FOREIGN PATENT DOCUMENTS

| CN | 1935089 A | 3/2007 |
| JP | 2004-517380 A | 6/2004 |

(Continued)

OTHER PUBLICATIONS

International Search Report issued Jan. 25, 2012 in PCT/JP2011/074932 filed Oct. 28, 2011.

(Continued)

*Primary Examiner* — Abolfazl Tabatabai
(74) *Attorney, Agent, or Firm* — Oblon, Spivak, McClelland, Maier & Neustadt, L.L.P.

(57) ABSTRACT

According to one embodiment, a medical image processing apparatus includes an image acquiring unit, a detection algorithm storage, an abnormal area detecting unit and an outputting unit. The image acquiring unit acquires image data of a corpse. The detection algorithm storage stores an abnormal area detection algorithm. The abnormal area detecting unit uses the abnormal area detection algorithm to the image data of the corpse and analyzes the image data to detect an abnormal area. The outputting unit outputs information of the abnormal area detected by the abnormal area detecting unit.

8 Claims, 8 Drawing Sheets

(56) References Cited

FOREIGN PATENT DOCUMENTS

JP  2005-034473 A  2/2005
JP  2011-004951 A  1/2011

OTHER PUBLICATIONS

Ihin Tou et al. "Precise Extraction of Cortical Bone from a 3D CT Imange for Autopsy Imagaing", Tokyo University of Agriculture and Technology, Chiba University, 2008, vol. 27, p. P16 (with English Abstract).

Seiji Shiotani et al., "AI (Autopsy Imagaing)", Journal of the Japan Association of Radiological Technologies, May 1, 2009, vol. 56, No. 5, pp. 459-169.

Toshiki Homma et al., "Anatomical Classification of Bones on 3D Chest CT Images Using a Digital Atlas of Human Anatomy", IEICE Techinical Report, Oct. 31, 2005, vol. 105, No. 386, pp. 63-68 (with English Abstract).

Seiji Shiotani et al., Autopsy Imaging (AI): Postmortem Imaging Findings, Dec. 25, 2009, vol. 30, No. 1, pp. 106-120.

International Preliminary Report on Patentability issued May 14, 2013 in PCT/JP2011/074932 filed Oct. 28, 2011 submitting English translation only.

Written Opinion issued Jan. 24, 2012 in PCT/JP2011/074932 filed Oct. 28, 2011 submitting English translation only.

Office Action issued Feb. 8, 2014 in Chinese Application No. 201180003611.6.

Seiji Shiotani, et al., "Postmortem computed tomography findings as evidence of traffic accident-related fatal injury", Radiat Med, vol. 26, 2008, pp. 253-260.

* cited by examiner

INFORMATION BY REGION

| REGION | | ABNORMAL AREA | IMAGE OF ABNORMAL AREA |
|---|---|---|---|
| A | HEAD | BLEEDING | slice $h_{30} \sim h_{40}$ |
| B | NECK | (NOT FOUND) | |
| C | BREAST | RIB FRACTURE | slice $c_{10} \sim c_{30}$ |
| D | ABDOMEN | (NOT FOUND) | |
| | ... | | |

FIG. 2A

COMMON INFORMATION UNRELATED TO REGIONS

| NAME | ○○△△ |
|---|---|
| AGE | 85 YEARS OLD |
| SEX | MALE |
| PREVIOUS ILLNESS / TIME ELAPSED AFTER ONSET / SYMPTOMS APPEARING IMMEDIATELY BEFORE DEATH | HYPERTENSION / 15 YEARS AGO UP TO PRESENT / APPEARING |
| CIRCUMSTANCES OF DEATH | IMMEDIATELY BEFORE, HEADACHE FOUND IN CARDIOPULMONARY ARREST AT BATHROOM OF HIS HOUSE |
| TIME ELAPSED AFTER DEATH | ABOUT TWO HOURS |
| WHETHER RESUSCITATION WAS DONE | DONE |
| PERFORMED RESUSCITATION | CARDIAC MASSAGE, INTRAVENOUS CATHETERIZATION |

FIG. 2B

| PREVIOUS ILLNESS | TIME ELAPSED AFTER ONSET OF PREVIOUS ILLNESS | SYMPTOMS APPEARING IMMEDIATELY BEFORE DEATH | REGION | FINDING | INFLUENCE LEVEL |
|---|---|---|---|---|---|
| HYPERTENSION | 15 YEARS AGO UP TO PRESENT | APPEARING | HEAD | INTRACEREBRAL HEMORRHAGE | 5 |
| BRUISE | TWO YEARS AGO | COMPLETELY CURED | LOWER LIMBS | (NOT FOUND) | 1 |
| PNEUMONIA | 20 YEARS AGO | COMPLETELY CURED | BREAST | (NOT FOUND) | 1 |
| | | | | | |

FIG. 6

| REGION | INFLUENCE LEVEL | EXCLUSION LEVEL | DISPLAY PRIORITY LEVEL | DISPLAY ORDER |
|---|---|---|---|---|
| HEAD | 5 | 12 | 41.7 | 1 |
| NECK | 1 | 100 | 1 | 4 |
| BREAST | 1 | 50 | 2 | 2 |
| ABDOMEN | 1 | 100 | 1 | 5 |
| UPPER LIMBS | 1 | 50 | 2 | 3 |
| LOWER LIMBS | 1 | 100 | 1 | 6 |

FIG. 8

| RADIOLOGIST NAME | SPECIALIZED REGION | TIME WHICH CAN BE WORKED |
|---|---|---|
| DOCTOR A | BREAST | EVERY FRIDAY: 4 P.M. TO 8 P.M. |
| DOCTOR B | ABDOMEN | EVERY THURSDAY: 3 P.M. TO 5 P.M. |
| DOCTOR C | HEAD | EVERY MONDAY: 6 P.M. TO 8 P.M. |
| ... | | |

FIG. 9

MEDICAL IMAGE PROCESSING APPARATUS

CROSS-REFERENCE TO RELATED APPLICATIONS

This application is a Continuation Application of No. PCT/JP2011/074932, filed on Oct. 28, 2011, and the PCT application is based upon and claims the benefit of priority from Japanese Patent Application No. 2010-243089, filed on Oct. 29, 2010, the entire contents of which are incorporated herein by reference.

FIELD

Embodiments described herein relate generally to a medical image processing apparatus for performing processing to ascertain the cause of death.

BACKGROUND

In recent years, Ai (Autopsy Imaging) has been adopted as a technique for ascertaining the causes of death of people. Ai is a procedure that diagnoses abnormalities such as a lesion and a wound that appeared while alive using post-mortal images taken by CT (Computed tomography) and MRI (Magnetic Resonance Imaging) to ascertain the cause of death.

Recently, since CT and MRI techniques have allowed fast image taking, it is recommended that an image of a whole body is taken in Ai by CT or MRI in order to ascertain the more accurate cause of death. Such imaging typically takes only about a few to a dozen or so minutes. However, because the number of resultant slice images of a whole body is a few thousand, which is enormous, it is considerably difficult for a radiologist to judge the cause of death from the images. In addition, it takes some time to display an enormous number of such images on a monitor.

In recent years, CAD (Computer-aided Detection/Diagnosis) has been put into practical use. CAD aids doctors in making diagnoses by detecting abnormal image areas (hereinafter, referred to as the abnormal areas) such as an abnormal area in an image created by a CT or an MRI apparatus. CAD is usually used for a living person. In order to diagnose a disease in a particular region such as a head, a breast, and an abdomen, CAD detects an abnormal area by using an algorithm suitable for the region on a taken image.

As mentioned above, in Ai, it is recommended to take an image of a whole body of a corpse in order to ascertain the cause of death. Therefore, the number of slice images becomes enormous, so that it is difficult for a radiologist to see all the slice images and judge the cause of death. In addition, because a corpse has characteristics which a living body does not have, a radiologist unfamiliar with image interpretation of a corpse may make an error in the determination of the cause of death.

If CAD is used for Ai, for example, CAD analyzes an enormous number of images of a whole body by using a different algorithm for each region from the head to the lower limbs in this order to detect an abnormal area. Then, CAD extracts all images including the abnormal area, thereafter presenting the images to a radiologist. In this case, it may take a considerable time, e.g., three or four days, to complete all the processes. Thus, disadvantageously, even if a radiologist desires to see only a part of a corpse, the radiologist needs to wait for the processing of a whole body to be completed.

Further, a corpse that underwent resuscitation before death may have an abnormality caused by influence of the resuscitation. In addition, a post-mortem change may occur in a corpse if some time has passed since the death. It is difficult to discriminate an abnormality that led to the cause of death from such a post-mortem change and abnormalities caused by resuscitation.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2A is a table illustrating an example of information by region stored in the information-by-region storage unit;

FIG. 2B is a table illustrating an example of common-to-region information stored in the common information storage unit;

FIG. 6 is a view illustrating an example of the influence levels;

FIG. 8 is a view illustrating an example of calculating a display priority level for each region; and FIG. 9 is a view illustrating an example of information stored in a radiologist characteristics database in a case where the information includes specialty of radiologists and medical specialists in the hospital or other hospitals specialize and times when the radiologists can interpret images.

DETAILED DESCRIPTION

Hereinbelow, a description will be given of a medical image processing apparatus according to embodiments of the present invention with reference to the drawings.

In general, according to one embodiment, a medical image processing apparatus includes an image acquiring unit, a detection algorithm storage, an abnormal area detecting unit and an outputting unit. The image acquiring unit acquires image data of a corpse. The detection algorithm storage stores an abnormal area detection algorithm. The abnormal area detecting unit uses the abnormal area detection algorithm to the image data of the corpse and analyzes the image data to detect an abnormal area. The outputting unit outputs information of the abnormal area detected by the abnormal area detecting unit.

Figure 1:
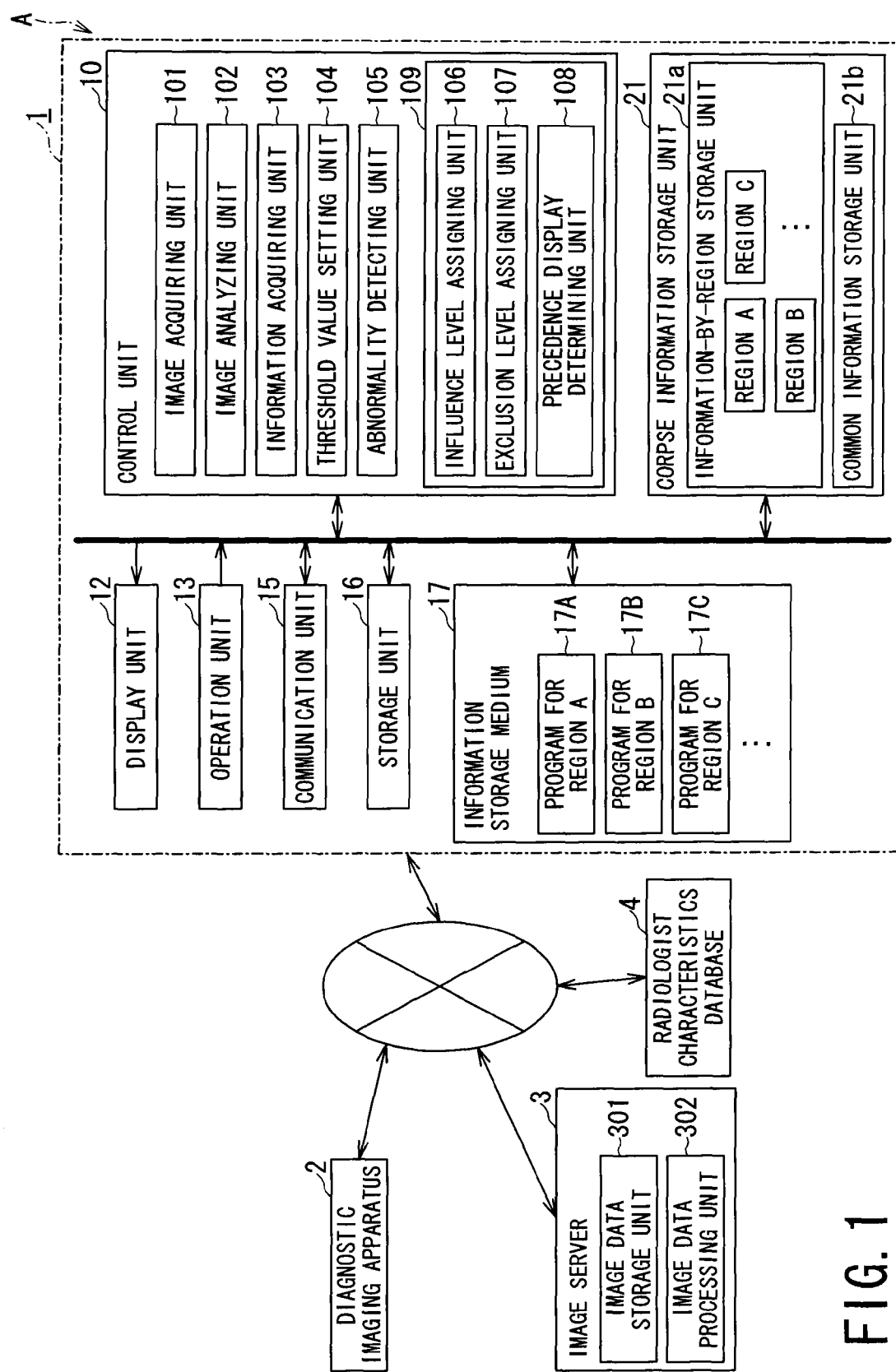
FIG. 1 is a schematic block diagram illustrating a medical information system according to an embodiment of the present invention.

FIG. 1 is a schematic block diagram illustrating a medical information system A according to an embodiment of the present invention. The medical information system A includes a medical image processing apparatus 1, a diagnostic imaging apparatus 2, an image server 3, and a radiologist characteristics database 4.

The diagnostic imaging apparatus 2 is an X-ray CT apparatus, an MRI apparatus, or the like. The diagnostic imaging apparatus 2 performs scans and takes images of a corpse X to carry out image processing. It is assumed that the diagnostic imaging apparatus 2 of the present embodiment is an X-ray CT apparatus.

The image server 3 is included in a PACS (Picture Archiving and Communication System), for example. The image server 3 includes an image data storage unit 301 and an image data processing unit 302. The image data storage unit 301 stores medical image data obtained by the diagnostic imaging apparatus 2 and IDs by region (e.g., "slice $h_1$" and "slice $c_1$"). The image data processing unit 302 classifies the image data stored in the image data storage unit 301 into each region on the basis of the IDs and outputs the image data in response to requests from the medical image processing apparatus 1.

The medical image processing apparatus 1 is installed as a part of an HIS (Hospital Information System), for example and connected to the diagnostic imaging apparatus 2 and the image server 3 via a LAN (local area network) in a hospital so that the apparatus 1 can communicate with the apparatus 2 and the server 3.

A radiologist characteristics database 4 stores regions in which radiologists and medical specialists in the hospital or other hospitals specialize and times when the radiologists can interpret images. FIG. 9 illustrates an example of stored information. Details will be described later.

The medical image processing apparatus 1 is based on a personal computer or a workstation that includes a CAD function. In the apparatus 1, a control unit 10, a display unit 12, an operation unit 13, a communication unit 15, a storage unit 16, an information storage medium 17, and a corpse information storage unit 21 are connected with each other via a bus so that they can communicate with each other.

The display unit 12 is a monitor, for example. The display unit 12 displays slice images described later and information associated with images. The operation unit 13 is a device such as a keyboard and a mouse, and inputs data. The communication unit 15 is connected to a LAN in a hospital and communicates with the diagnostic imaging apparatus 2 or the image server 3. The storage unit 16 functions as a work area for the control unit 10 and the communication unit 15 and can be provided by RAM (Random Access Memory) or the like.

The information storage medium 17 (computer-readable medium) is used to store programs and data, and can be provided by a hard disk drive, memory (Flash Memory or ROM (Read Only Memory)), or the like. Also, in the information storage medium 17, programs for causing a computer to function as each unit in the present embodiment (programs that cause the computer to perform processing of each unit) and CAD programs for detecting an abnormal area which are a program 17A for a region A, a program 17B for a region B, a program 17C for a region C, and so on are stored.

The control unit 10 is an arithmetic unit that performs overall control as well as various types of arithmetic and control processing. The functions of the control unit 10 can be provided by hardware such as various processors (a CPU, a DSP, etc.) and ASIC (a gate array etc.) and by programs. The control unit 10 performs a variety of processes in the present embodiment on the basis of the programs (data) stored in the information storage medium 17.

Also, the control unit 10 includes an image acquiring unit 101, an image analyzing unit 102, an information acquiring unit 103, a threshold value setting unit 104, and an abnormality detecting unit (abnormal area detecting unit) 105. In addition, the control unit 10 includes an influence level assigning unit 106, an exclusion level assigning unit 107, and a precedence display determining unit 108, as an outputting unit 109. The influence level assigning unit 106, the exclusion level assigning unit 107, and the precedence display determining unit 108 function as the outputting unit and output information of an abnormal area detected by the abnormality detecting unit 105 to display the information on the display unit 12.

The image acquiring unit 101 acquires medical image data stored in the image server 3. The image analyzing unit 102 analyzes an image of the medical image data acquired by the image acquiring unit 101 on the basis of the programs 17A, 17B, 17C and so on for the particular regions, the programs being stored in the information storage medium 17.

The abnormality detecting unit 105 detects an abnormal area having a close relationship to the cause of death on the basis of the image analyzed by the image analyzing unit 102. Also, the abnormality detecting unit 105 may extract an abnormal area that is estimated to be caused by post-mortem change or resuscitation and exclude this area in detection of an abnormal area having a close relationship to the cause of death.

The information acquiring unit 103 acquires various types of information stored in the corpse information storage unit 21. The threshold value setting unit 104 sets parameters such as a threshold value of a size of an air in a cranium if information of resuscitation described later is "done."

The influence level assigning unit 106 and the exclusion level assigning unit 107 of the outputting unit 109 calculate respectively levels of influence and exclusion to and from the cause of death, described later. The precedence display determining unit 108 of the outputting unit 109 determines order of regions to be displayed on the display unit 12. The outputting unit 109 displays on the display unit 12 an image of an abnormal area from which an abnormal area being estimated to be caused by post-mortem change or resuscitation is excluded. Alternatively, the outputting unit 109 displays on the display unit 12 an abnormal area being estimated to be caused by post-mortem change or resuscitation in a displaying manner different from that of other areas so that the area can be easily distinguished from the other areas (e.g., changing a color into one different from that of other areas). Details will be described later.

The corpse information storage unit 21 includes an information-by-region storage unit 21a and a common information storage unit 21b. In the storage unit 21a, as information classified by region, an abnormal area detected by the abnormality detecting unit 105 and IDs of image data corresponding to the abnormal area are stored for each of the regions A, B, C and so on. In the storage unit 21b, common information unrelated to the regions is stored.

FIG. 2A is a table illustrating an example of information by region stored in the information-by-region storage unit 21a. FIG. 2B is a table illustrating an example of common-to-region information stored in the common information storage unit 21b.

In the example of FIG. 2A, information of "head" is stored in the region A, where an abnormal area detected by the abnormality detecting unit 105 is "bleeding" and IDs of image data photographing the abnormal area are "slice $h_{30}$" to "slice $h_{40}$." Also, in each of the other regions, an abnormal area detected by the abnormality detecting unit 105 (if an abnormal area is not found, "not found" is recorded) and IDs of image data are stored.

In the example of FIG. 2B, the common-to-region information stored in the common information storage unit 21b is information of a corpse X. The information includes X's name, age, and sex, a previous illness, time elapsed after the onset of the previous illness, symptoms appearing immediately before the death, circumstances of the death, time elapsed after the death, the fact whether resuscitation is performed, and the performed resuscitation. Since these information items are not associated directly with regions, the items are separately stored as common-to-region information.

<Operation for Extracting Image of Abnormal Area>

Figure 3:
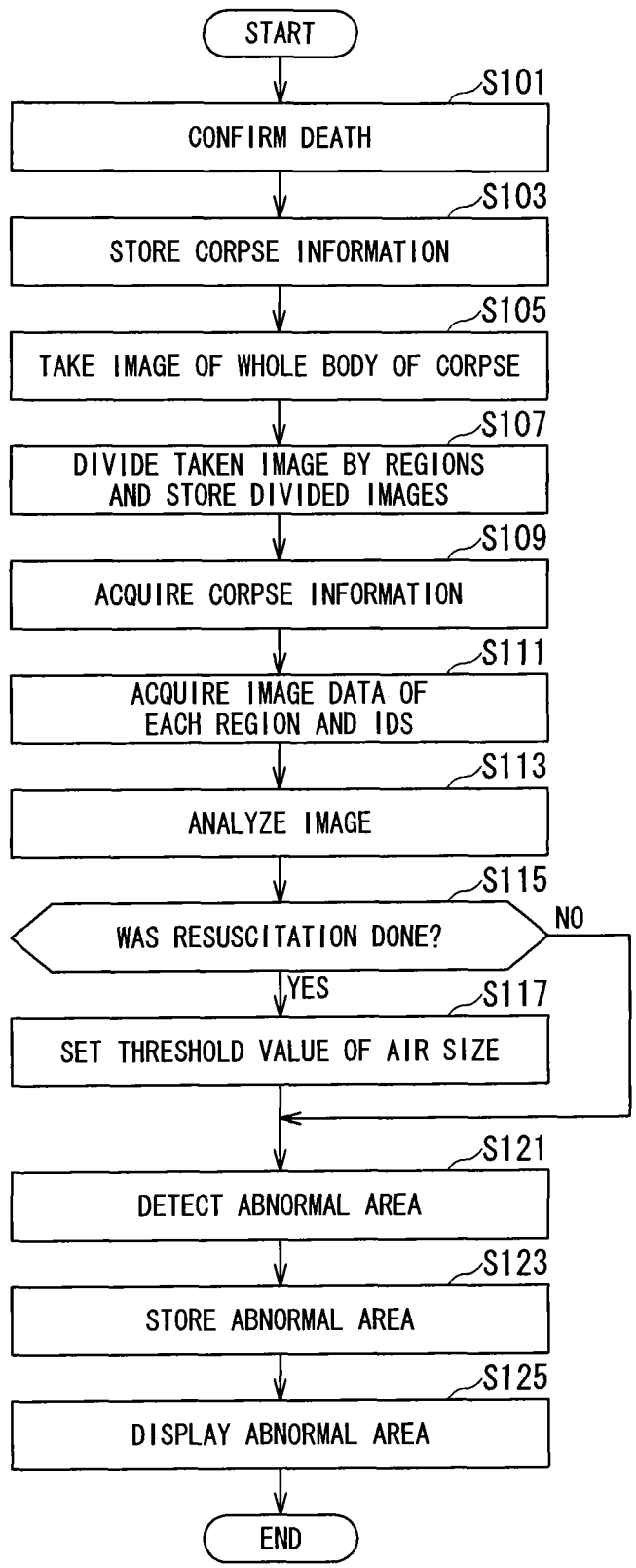
FIG. 3 is a flow chart illustrating a procedure in extracting an image of an abnormal area to ascertain the cause of death by the medical information system.

Next, an operation of the medical information system A described above will be described with reference to FIG. 3. The operation is used for extracting an image of an abnormal area to ascertain the cause of death. In the present embodiment, a description will be made using the common-to-region information of the corpse X as illustrated in FIG. 2B.

First, a doctor confirms the death of a corpse X who suffered a cardiopulmonary arrest at the bathroom of X's house and was transported to a hospital by ambulance (step S141). The doctor then finds out a name, an age, and circumstances of the death of the corpse X from the family having lived with X, in order to ascertain the cause of death, and inputs the information from the family into the medical image processing apparatus 1. The doctor also inputs the fact whether resuscitation was performed, the performed resuscitation, and time elapsed after the death. Since the input information is unrelated to regions, the medical image processing apparatus 1 stores the common-to-region information of the corpse X, input from the operation unit 13, into the common information storage unit 21b of the corpse information storage unit 21 (step S103).

Next, the diagnostic imaging apparatus 2 takes an image of a whole body of the corpse X (step S105). Then, the diagnostic imaging apparatus 2 divides the taken image data by regions, assigns image IDs to the divided images by regions, and stores the images into the image data storage unit 301 of the image server 3 (step S107).

Next, the information acquiring unit 103 of the medical image processing apparatus 1 acquires the common-to-region information, which is unrelated to the regions of the corpse X and stored in the common information storage unit 21b in step S103 (step S109). When corpse information is acquired, if the person has been treated at a hospital while alive and a medical record of a patient corresponding to the corpse X is held in a patient information database of the hospital where the person died, or the medical record of the patient corresponding to the corpse X is held in a patient information database of another hospital and available via a network, the information acquiring unit 103 may acquire a name, an age, a sex, and a previous illness of the corpse from such a patient information database. Alternatively, if a paper patient's chart is available, the chart may be input into the medical image processing apparatus 1 directly or by OCR (Optical Character Reader).

Next, the image acquiring unit 101 acquires the image data of each region of the corpse X and the IDs stored in the image data storage unit 301 of the image server 3 (step S111). Then, the image analyzing unit 102 analyzes each of the image data items of the corpse X, the image data items being acquired in step S111 and classified by regions, by using the CAD program for each region (the program 17A for the region A, the program 17B for the region B, the program 17C for the region C, and so on), stored in the information storage medium 17 (step S113).

The image analysis is a known technique. An air, a bone, and the like can be determined from CT values (Hounsfield number; a unit is Hounsfield Unit [HU]) identified by the image analysis. For example, the CT value of the cranium is 500 HU, but if a shadow of −1000 HU is inside a continuous series of shadows having the CT value of 500 HU, it can be determined that the shadow of −1000 HU is an air. Also, if there is a discontinuous point in a continuous series of shadows having the CT value of 500 HU, it can be determined that there is a fracture of a bone.

Now, since an abnormal area caused by resuscitation is not associated directly with the cause of death, such an abnormal area needs to be excluded from detected abnormal areas. For example, resuscitation of a cardiac massage may cause abnormalities such as a rib fracture and fine airs in the cranium, so that these abnormalities need to be excluded from the cause of death.

Thus, the information acquiring unit 103 determines whether resuscitation was done from the common-to-region information of the corpse X acquired by the common information storage unit 21b in step S109. If the resuscitation was "done" (yes in step S115), the threshold value setting unit 104 sets a threshold value of an air size, for example (step S117). In addition to the setting of a threshold value of an air size, the threshold value setting unit 104 can also set parameters for determining whether an abnormal area is postmortem hypostasis of a post-mortem change or bleeding that occurred while alive. The determination is made on the basis of the time elapsed after the death acquired by the information acquiring unit 103 from the common information storage unit 21b in step S109.

Next, the abnormality detecting unit 105 excludes an air smaller than the threshold value set by the threshold value setting unit 104 from the image data of each region analyzed by the image analyzing unit 102 in steps S113 to S117, thereby detecting an abnormal area (step S121). For example, if an area (shadow) of −1000 HU is smaller than a set threshold value, the abnormality detecting unit 105 excludes the area (shadow) and if larger than the threshold value, the abnormality detecting unit 105 detects the area as an abnormal area.

Next, the control unit 10 extracts the information of the abnormal area detected by the abnormality detecting unit 105 and IDs of the image data corresponding to the abnormal area. Then, the control unit 10 stores them in the information-by-region storage unit 21a of the corpse information storage unit 21 (step S123).

It should be noted that if a doctor visually judges an abnormal area of an image without using the image analysis of CAD, the doctor may input the information of the abnormal area and IDs of image data corresponding to the abnormal area into the medical image processing apparatus 1. The control unit 10 stores the input information into the information-by-region storage unit 21a.

Next, if the doctor instructs the medical image processing apparatus 1 through the operation unit 13 to display a particular region, the control unit 10 causes the image data processing unit 302 to output image data in the image data storage unit 301 and display the data on the display unit 12, on the basis of the IDs of the image data corresponding to the abnormal area in the region, the IDs being stored in the information-by-region storage unit 21a in step S123. In addition, the control unit 10 simultaneously displays on the display unit 12 the common-to-region information of the corpse X stored in the common information storage unit 21b (step S125).

Since the number of image data sheets chosen when an abnormal area is detected in step S121 is substantially limited due to the setting of a threshold value in step S117, all the images can be significant to ascertain the cause of death, so that the doctor examines all the images to determine the cause of death.

Figure 4:
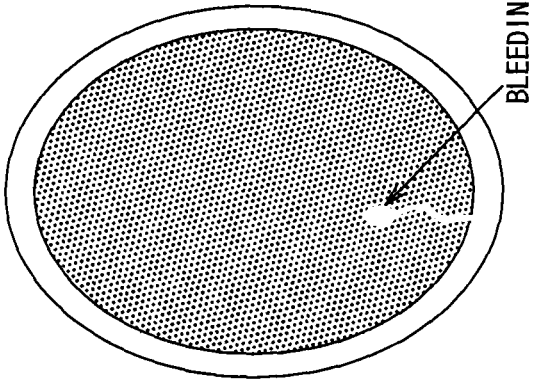
FIG. 4 is a view illustrating an example in which a head image is displayed on the display unit.

FIG. 4 illustrates an example in which a head image is displayed on the display unit 12. In FIG. 4, the head is selected with one of right side buttons. Further, "slice $h_{35}$" of images of the head and common-to-region information of a corpse X are displayed. In "slice $h_{35}$," an abnormal area is detected, and the common-to-region information is stored in the common information storage unit 21*b*. In the head image, the abnormal area determined as a bleeding using a CT value can be confirmed. Note that an air caused by resuscitation is not displayed since the air has been excluded from the abnormal areas.

<Operation to Decide Region to be Preferentially Displayed>

Figure 5:
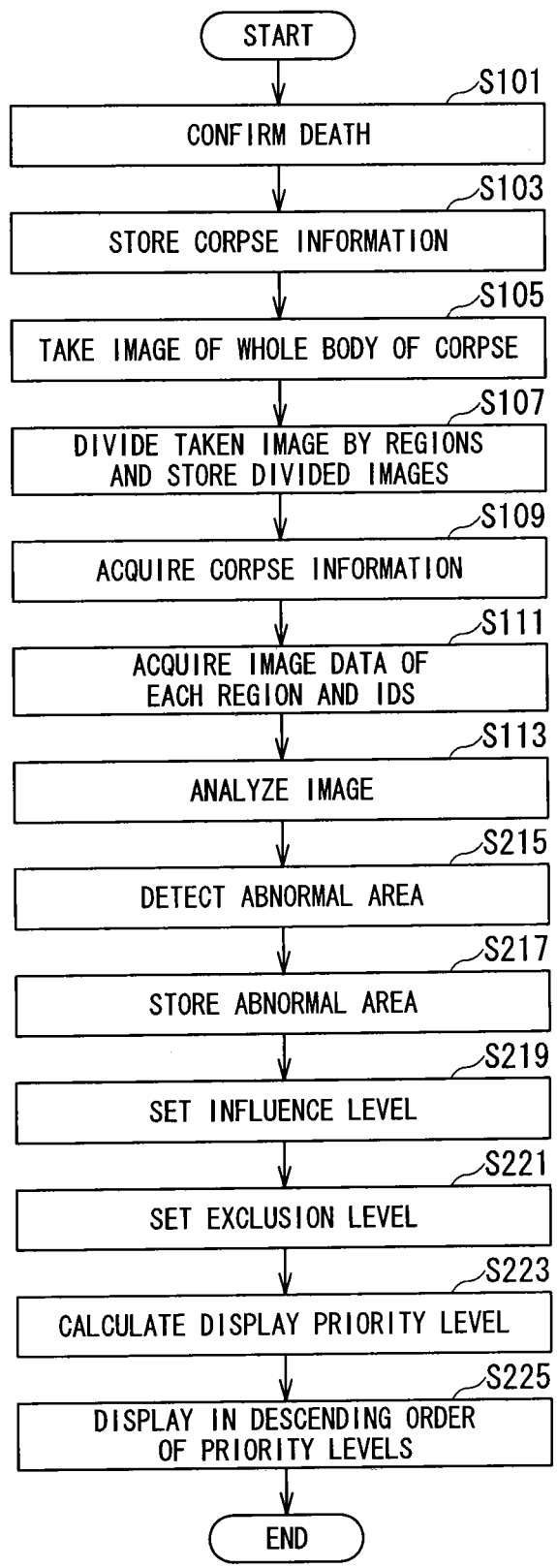
FIG. 5 a flow chart illustrating a procedure in determining a region to be preferentially displayed in ascertaining the cause of death by the medical information system.

As another example, another operation of the medical information system A described above will be described with reference to FIG. 5. The operation is used for determining a region to be preferentially displayed in ascertaining the cause of death. Also in the present embodiment, a description will be made using the common-to-region information of the corpse X as illustrated in FIG. 2B.

Because the flow of confirming death to image analysis that uses CAD is identical to step S101 to S113 described above, a description thereof will be omitted. Now, the abnormality detecting unit 105 detects abnormal areas from the image data of each region, the data being analyzed by the image analyzing unit 102 in step S113 (step S215). At this time, all the abnormal areas including ones caused by resuscitation are detected as findings obtained by CAD. Next, the control unit 10 extracts the abnormal areas detected by the abnormality detecting unit 105 and IDs of the image data corresponding to the abnormal areas. Then, the control unit 10 stores them in the information-by-region storage unit 21*a* of the corpse information storage unit 21 (step S217).

Now, the influence level assigning unit 106 in the control unit 10 assigns a level of influence on the cause of death to findings or a previous illness of each region (step S219). The influence level assigning is based on a previous illness, time elapsed after the onset of the previous illness, and symptoms appearing immediately before the death, which have been acquired by the information acquiring unit 103 in step S109 and the abnormal areas (findings) of each region, detected in step S215 (Step S219).

FIG. 6 illustrates an example of the influence levels. The influence levels have been set in advance on the basis of a number of previous illnesses and lesions (findings) caused by the previous illnesses, and stored in the storage unit 16. As an example of setting of influence levels in the storage unit 16, the levels are represented in numbers from "5" to "1" on a five-point scale in descending order of the influence on the cause of death.

For example, in FIG. 6, a previous illness "hypertension" of the corpse X and a finding "intracerebral hemorrhage" stored in the common information storage unit 21*b* have a close relationship to the cause of death since it is believed that the hypertension from which the patient was suffering caused the intracerebral hemorrhage, so that the influence level assigning unit 106 assigns "5" to the influence level. On the other hand, because the previous illness "pneumonia" occurred 20 years ago and had been completely cured by the time immediately before the death, the previous illness has little influence on the cause of death, so that the influence level assigning unit 106 assigns "1" to the influence level. It should be noted that even if there is no previous illness, a high influence level may be assigned with only findings. For example, in a corpse of a victim of a fatal traffic accident, if a finding is "rupture of the viscera," only the finding has a high level of influence on the cause of death even without a previous illness, a high influence level is assigned.

Also, the influence level assigning unit 106 may automatically calculate an influence level of each lesion that can be caused by a previous illness, on the cause of death. In this case, the influence level assigning unit 106 acquires from a medical server, for example, a previous illness of a patient, time elapsed after the onset of the previous illness, and information of symptoms appearing immediately before the death (e.g., appearing or completely cured). Next, the influence level assigning unit 106 assigns a basic point according to the likelihood of death to each of lesions that can be caused by each of the previous illnesses. Next, the influence level assigning unit 106 weights the basic point in accordance with the time elapsed after the onset of the previous illness and the symptoms appearing immediately before the death, thereby calculating a level of influence on the cause of death of each of the lesions that can be caused by a previous illness. Then, the influence level assigning unit 106 assigns the calculated level of influence on the cause of death to the finding of each region or previous illness (see FIG. 6).

Next, the exclusion level assigning unit 107 in the control unit 10 assigns a level of exclusion from the cause of death to the finding of each region on the basis of the performed resuscitation and the time elapsed after the death, acquired by the information acquiring unit 103 in step S109 as well as on the basis of the abnormal area (finding) of each region detected in step S215 (step S221).

Figure 7:
FIG. 7 is a view illustrating an example of the exclusion levels.

FIG. 7 illustrates an example of the exclusion levels. The exclusion levels are set in advance on the basis of relationships between lesions (findings) and performed resuscitations or times elapsed after death (information to be excluded from the cause of death) and stored in the storage unit 16. As an example of setting of exclusion levels in the storage unit 16, the levels are graded with 100, 50, 10, and 1 points in descending order of the relationships, namely, in ascending order of relationships to the cause of death. If there are multiple items of relevant "information to be excluded from the cause of death" to one finding, points of exclusion levels set in accordance with a relationship between each item of the "information to be excluded from the cause of death" and the finding are summed up.

In FIG. 7, for example, exclusion levels of information to be excluded from the cause of death, i.e., "cardiac massage," "intravenous catheterization," and "two hours elapsed after the death" are "1," "10," and "1," respectively. The exclusion levels are graded according to the relationships with the finding of the head, "air in the cranium," and the information to be excluded from the cause of death and the finding are stored in the common information storage unit 21*b*. The sum of the points is 12 and the exclusion level assigning unit 107 assigns 12 to the finding "air in the cranium." Further, since a finding of the breast, "rib fracture," has an exclusion level of "50" assigned based on a relationship to "cardiac massage" being information to be excluded from the cause of death, the exclusion level assigning unit 107 assigns "50" to the finding "rib fracture."

Next, the precedence display determining unit 108 calculates a display priority level of each region on the basis of the influence level assigned in step S219 and the exclusion level assigned in step S221 (step S223). Then, the precedence display determining unit 108 displays the regions in descending order of the display priority levels calculated in step S223 on the display unit 12 (step S225).

It should be noted that in the example described in the present embodiment, an influence level and an exclusion level are assigned for each region, but an influence level and an exclusion level may be assigned for each abnormal area and each slice. For example, if an influence level and an exclusion level are assigned for each slice, the precedence display determining unit 108 calculates a display priority level for each slice including an abnormal area. Also, if an influence level and an exclusion level are assigned for each abnormal area, the precedence display determining unit 108 calculates a display priority level for each abnormal area.

FIG. 8 illustrates an example of calculating a display priority level for each region. For the corpse X, display priority levels are calculated by the following equation (1) using the level of influence ("5" to "1") on the cause of death, assigned to each region in step S219, and the level of exclusion, for example, ("100," "50," "10," and "1" points) to be excluded from the cause of death, assigned to each region in step S221.

Display Priority Level=(Influence Level/Exclusion Level)×100     (1)

The display priority level indicates that as a number is larger, the region of interest may have a closer relationship to the cause of death. As a result, a doctor preferentially interprets a region with a higher display priority level, thereby allowing early judgment of the cause of death.

In FIG. 8, among the regions, the head and the breast have higher display priority levels, so that the precedence display determining unit 108 displays the head and the breast on the display unit 12 in this order. A doctor sequentially examines images of these regions to judge the cause of death. It should be noted that regions displayed on the display unit 12 by the precedence display determining unit 108 may be, for example, three regions having the highest three display priority levels or only regions having display priority levels higher than a predetermined value. If a plurality of regions have the same display priority level, a region closer to one of the head and the lower limbs may be displayed first.

<Case of Determining Region to which Image Analysis is Preferentially Performed and Displayed Based on Radiologist Information>

In step S113, a CAD program for each region has been used to perform image analysis of each of the regions in parallel or in order from the head to the lower limbs, or in order from the lower limbs to the head, but with reference to the radiologist characteristics database 4 illustrated in FIG. 9, the order in which regions receive image analysis can be set on the basis of the convenience of radiologists. This is effective if a remote X-ray interpretation service is used and a remote radiologist specializing in a region interprets an image or if a time period for image interpretation is limited because of a time constraint of a doctor. In the flow chart of FIG. 3, the image analyzing unit 102 refers to the radiologist characteristics database 4 in the image analysis in step S113, to perform the image analysis of a region specialized by a radiologist who can work first, then displaying an abnormal area of the region.

As hereinbefore described, in order to ascertain the cause of death, the present invention takes images of a corpse X to obtain images of each region, and analyzes each region by CAD to detect an abnormal area. If the corpse X has received resuscitation, a threshold value is set and an abnormal area caused by the resuscitation is excluded. Then, only images in which an abnormal area is detected are displayed for each region. As a result, the cause of death can be efficiently ascertained.

In addition, in light of a previous illness and resuscitation, a level of influence on the cause of death and a level of exclusion from the cause of death are assigned to each region, and thereby a display priority level of each region is determined. As a result, a region to be preferentially interpreted is found out, which thereby helps the cause of death to be determined early.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
   an image acquiring unit configured to acquire image data of a corpse;
   a detection algorithm storage unit in which an abnormal area detection algorithm is stored;
   an abnormal area detecting unit configured to apply the abnormal area detection algorithm to the image data of the corpse and analyze the image data to detect an abnormal area, wherein the abnormal area detecting unit is further configured to determine a level of influence on a cause of death by using at least one of previous illness information of the corpse, time information elapsed after the death, a symptom that appears immediately before the death and resuscitation information; and
   an outputting unit configured to output information of the abnormal area detected by the abnormal area detecting unit.

2. The medical image processing apparatus according to claim 1, wherein the abnormal area detecting unit detects an abnormal area having a close relationship to the cause of death.

3. The medical image processing apparatus according to claim 1, wherein the abnormal area detecting unit excludes an abnormal area estimated to be caused by resuscitation.

4. The medical image processing apparatus according to claim 3, wherein the abnormal area detecting unit assigns an exclusion level which indicates a level of information to be excluded from the cause of death and which becomes higher when a relationship between information of an abnormal area of each region and the resuscitation information is closer.

5. The medical image processing apparatus according to claim 1, wherein the abnormal area detecting unit detects the abnormal area by using at least one of the previous illness information of the corpse, the symptom that appears immediately before the death, and the resuscitation information.

6. The medical image processing apparatus according to claim 1, wherein the outputting unit sets a priority of display output of image data based on the level of influence.

7. The medical image processing apparatus according to claim 6, wherein
   the detection algorithm storage unit stores a plurality of abnormal area detection algorithms associated with different regions, and
   the abnormality detecting unit changes the abnormal area detection algorithm depending upon a region of image data.

8. The medical image processing apparatus according to claim 1, wherein
   the abnormal area detecting unit extracts an abnormal area being estimated to be caused by resuscitation or post-mortem change, and
   the outputting unit displays the abnormal area being estimated to be caused by resuscitation or post-mortem change in a displaying manner different from that of another area.

* * * * *